US00RE43009E

(19) United States
(12) Reissued Patent
Chornenky et al.

(10) Patent Number: US RE43,009 E
(45) Date of Reissued Patent: Dec. 6, 2011

(54) APPARATUS AND METHOD FOR REDUCING SUBCUTANEOUS FAT DEPOSITS BY ELECTROPORATION

(75) Inventors: Victor I. Chornenky, Minnetonka, MN (US); Ali Jaafar, Eden Prairie, MN (US)

(73) Assignee: AngioDynamics, Inc., Latham, NY (US)

(21) Appl. No.: 12/572,005

(22) Filed: Oct. 1, 2009

Related U.S. Patent Documents

Reissue of:

(64) Patent No.: 6,795,728
Issued: Sep. 21, 2004
Appl. No.: 10/369,020
Filed: Feb. 19, 2003

U.S. Applications:

(63) Continuation-in-part of application No. 09/931,672, filed on Aug. 17, 2001, now Pat. No. 6,892,099.

(60) Provisional application No. 60/358,443, filed on Feb. 22, 2002, provisional application No. 60/267,106, filed on Feb. 8, 2001, provisional application No. 60/225,775, filed on Aug. 17, 2000.

(51) Int. Cl.
*A61N 1/18* (2006.01)

(52) U.S. Cl. ..... 607/2; 607/72

(58) Field of Classification Search ..... 607/2, 3, 607/72, 115, 116, 148, 152, 153; 600/373–375, 600/377, 378, 381; 604/20; 128/907
See application file for complete search history.

(56) References Cited

U.S. PATENT DOCUMENTS

| | | | |
|---|---|---|---|
| 1,653,819 | A | 12/1927 | Northcott et al. |
| 4,016,886 | A | 4/1977 | Doss |
| 4,226,246 | A | 10/1980 | Fragnet |
| 4,262,672 | A | 4/1981 | Kief |
| 4,407,943 | A | 10/1983 | Cole et al. |
| 4,810,963 | A | 3/1989 | Blake-Coleman et al. |
| 4,907,601 | A | 3/1990 | Frick |
| 4,946,793 | A | 8/1990 | Marshall, III |
| 5,019,034 | A | 5/1991 | Weaver et al. |
| 5,052,391 | A | 10/1991 | Silberstone et al. |
| 5,058,605 | A | 10/1991 | Slovak |
| 5,098,843 | A | 3/1992 | Calvin |

(Continued)

FOREIGN PATENT DOCUMENTS

| | | |
|---|---|---|
| DE | 863111 | 1/1953 |

(Continued)

OTHER PUBLICATIONS

Amasha, et al., Quantitative Assessment of Impedance Tomography for Temperature Measurements in Microwave Hyperthermia, *Clin. Phys. Physiol. Meas.*, 1998, Suppl. A, 49-53.

(Continued)

*Primary Examiner* — Scott Getzow
(74) *Attorney, Agent, or Firm* — Harry K. Ahn; Abelman Frayne & Schwab

(57) ABSTRACT

An apparatus and method for minimally invasive treatment of deep subcutaneous fat deposits in lieu of cosmetic surgery is disclosed. The apparatus comprises a high voltage pulse generator connected to two or more needle electrodes at least one of which is configured for placement deeply under the skin in a treatment site of the patient's body. High voltage pulses, delivered to the electrodes, create an electric field that kills subcutaneous fat cells.

24 Claims, 6 Drawing Sheets

U.S. PATENT DOCUMENTS 5,134,070 A 7/1992 Casnig
5,173,158 A 12/1992 Schmukler
5,193,537 A 3/1993 Freeman
5,273,525 A 12/1993 Hofmann
5,283,194 A 2/1994 Schmukler
5,318,563 A 6/1994 Malis et al.
5,328,451 A 7/1994 Davis et al.
5,389,069 A 2/1995 Weaver
5,403,311 A 4/1995 Abele et al.
5,425,752 A 6/1995 Vu'Nguyen
5,439,440 A 8/1995 Hofmann
5,458,625 A 10/1995 Kendall
5,533,999 A 7/1996 Hood et al.
5,536,240 A 7/1996 Edwards et al.
5,575,811 A 11/1996 Reid et al.
5,626,146 A 5/1997 Barber et al.
5,634,899 A 6/1997 Shapland et al.
5,674,267 A 10/1997 Mir et al.
5,702,359 A 12/1997 Hofmann
5,720,921 A 2/1998 Meserol
5,778,894 A 7/1998 Dorogi et al.
5,782,882 A 7/1998 Lerman et al.
5,800,378 A 9/1998 Edwards et al.
5,810,762 A 9/1998 Hofmann
5,836,905 A 11/1998 Lemelson et al.
5,843,026 A 12/1998 Edwards et al.
5,873,849 A 2/1999 Bernard
5,919,142 A 7/1999 Boone et al.
5,947,889 A 9/1999 Hehrlein
5,983,131 A 11/1999 Weaver et al.
5,991,697 A 11/1999 Nelson et al.
5,999,847 A 12/1999 Elstrom
6,009,347 A 12/1999 Hofmann
6,010,613 A 1/2000 Walters et al.
6,016,452 A 1/2000 Kasevich
6,041,252 A * 3/2000 Walker et al. ..... 604/20
6,055,453 A 4/2000 Hofmann et al.
6,068,650 A 5/2000 Nanda et al.
6,085,115 A 7/2000 Weaver et al.
6,090,106 A 7/2000 Goble et al.
6,102,885 A 8/2000 Bass
6,106,521 A 8/2000 Blewett et al.
6,109,270 A 8/2000 Mah et al.
6,122,599 A 9/2000 Mehta
6,132,419 A 10/2000 Hofmann
6,159,163 A 12/2000 Strauss et al.
6,208,893 B1 3/2001 Hofmann
6,210,402 B1 4/2001 Olsen et al.
6,212,433 B1 4/2001 Behl
6,216,034 B1 4/2001 Hofmann
6,219,577 B1 4/2001 Brown et al.
6,241,702 B1 6/2001 Lundquist et al.
6,261,831 B1 7/2001 Agee
6,278,895 B1 8/2001 Bernard
6,300,108 B1 10/2001 Rubinsky
6,326,177 B1 12/2001 Schoenbach et al.
6,347,247 B1 2/2002 Dev et al.
6,349,233 B1 2/2002 Adams
6,351,674 B2 2/2002 Silverstone
6,387,671 B1 5/2002 Rubinsky et al.
6,403,348 B1 6/2002 Rubinsky et al.
6,470,211 B1 10/2002 Ideker et al.
6,482,619 B1 11/2002 Rubinsky et al.
6,493,592 B1 12/2002 Leonard et al.
6,500,173 B2 12/2002 Underwood et al.
6,526,320 B2 2/2003 Mitchell
6,562,604 B2 5/2003 Rubinsky et al.
6,607,529 B1 8/2003 Jones et al.
6,611,706 B2 8/2003 Avrahami et al.
6,613,211 B1 9/2003 McCormick et al.
6,627,421 B1 9/2003 Unger et al.
6,653,091 B1 11/2003 Dunn et al.
6,669,691 B1 12/2003 Taimisto
6,678,558 B1 * 1/2004 Dimmer et al. ..... 607/3
6,692,493 B2 2/2004 McGovern et al.
6,697,669 B2 2/2004 Dev et al.
6,697,670 B2 2/2004 Chomenky et al.
6,702,808 B1 3/2004 Kreindel
6,795,728 B2 9/2004 Chornenky et al.
6,801,804 B2 10/2004 Miller et al.
6,865,416 B2 3/2005 Dev et al.
6,892,099 B2 5/2005 Jaafar et al.
6,912,417 B1 6/2005 Bernard et al.
6,927,049 B2 8/2005 Rubinsky et al.
6,962,587 B2 11/2005 Johnson et al.
6,972,014 B2 12/2005 Eum et al.
6,994,706 B2 2/2006 Chornenky et al.
7,053,063 B2 5/2006 Rubinsky et al.
7,063,698 B2 6/2006 Whayne et al.
7,130,697 B2 10/2006 Chornenky et al.
7,211,083 B2 5/2007 Chornenky et al.
7,267,676 B2 9/2007 Chornenky et al.
2001/0044596 A1 11/2001 Jaafar
2002/0010491 A1 1/2002 Schoenbach
2002/0055731 A1 5/2002 Atala et al.
2002/0077676 A1 6/2002 Schroeppel et al.
2002/0099323 A1 7/2002 Dev et al.
2002/0138117 A1 9/2002 Son
2002/0193831 A1 12/2002 Smith, III
2003/0009110 A1 1/2003 Tu et al.
2003/0060856 A1 3/2003 Chornenky et al.
2003/0088189 A1 5/2003 Tu et al.
2003/0130711 A1 7/2003 Pearson et al.
2003/0170898 A1 9/2003 Gundersen et al.
2003/0208200 A1 11/2003 Palanker et al.
2003/0225360 A1 12/2003 Eppstein et al.
2004/0019371 A1 1/2004 Jaafar et al.
2004/0059389 A1 3/2004 Chornenky et al.
2004/0146877 A1 7/2004 Diss et al.
2004/0153057 A1 8/2004 Davison
2004/0243107 A1 12/2004 Macoviak
2004/0267189 A1 12/2004 Mavor et al.
2005/0043726 A1 2/2005 McHale et al.
2005/0049541 A1 3/2005 Behar et al.
2005/0165393 A1 7/2005 Eppstein
2005/0171523 A1 8/2005 Rubinsky et al.
2005/0171574 A1 8/2005 Rubinsky et al.
2005/0182462 A1 8/2005 Chornenky et al.
2005/0261672 A1 11/2005 Deem et al.
2005/0288730 A1 12/2005 Deem et al.
2006/0015147 A1 1/2006 Persson et al.
2006/0025760 A1 2/2006 Podhajsky
2006/0079883 A1 4/2006 Elmouelhi et al.
2006/0121610 A1 6/2006 Rubinsky et al.
2006/0212078 A1 9/2006 Demarais et al.
2006/0217703 A1 9/2006 Chornenky et al.
2006/0264752 A1 11/2006 Rubinsky et al.
2007/0043345 A1 2/2007 Davalos et al.
2007/0118069 A1 5/2007 Persson et al.
2008/0052786 A1 2/2008 Lin et al.

FOREIGN PATENT DOCUMENTS

DE 4000893 7/1991
EP 0378132 7/1990
EP 0935482 5/2005
WO 9639531 12/1996
WO 0020554 4/2000
WO 0107583 2/2001
WO 0107584 2/2001
WO 0107585 2/2001
WO 0181533 11/2001
WO 04037341 5/2004

OTHER PUBLICATIONS

Andreason, Electroporation as a Technique for the Transfer of Macromolecules into Mammalian Cell Lines, *J. Tiss. Cult. Meth.,* 15:56-62, 1993.

Baker, et al., Calcium-Dependent Exocytosis in Bovine Adrenal Medullary Cells with Leaky Plasma Membranes, *Nature,* vol. 276, pp. 620-622, 1978.

Barber, Electrical Impedance Tomography Applied Potential Tomography, Advances in Biomedical Engineering, Beneken and Thevenin, eds., IOS Press, 1993.

Beebe, S.J., et al., Nanosecond pulsed electric field (nsPEF) effects on cells and tissues: apoptosis induction and tumor growth inhibition.

PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.
Blad, et al., Impedance Spectra of Tumour Tissue in Comparison with Normal Tissue; a Possible Clinical Application for Electrical Impedance Tomography, *Physiol. Meas.* 17 (1996) A105-A115.
Bown, S.G., Phototherapy of tumors. *World J. Surgery*, 1983. 7: p. 700-9.
BPH Management Strategies: Improving Patient Satisfaction, *Urology Times,* May 2001, vol. 29, Supplement 1.
Brown, et al., Blood Flow Imaging Using Electrical Impedance Tomography, *Clin. Phys. Physiol. Meas.,* 1992, vol. 13, Suppl. A, 175-179.
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Coates, C.W.,et al., "The Electrical Discharge of the Electric Eel, Electrophorous Electricus," Zoologica, 1937, 22(1), pp. 1-32.
Cook, et al., ACT3: A High-Speed, High-Precision Electrical Impedance Tomograph, *IEEE Transactions on Biomedical Engineering,* vol. 41, No. 8, Aug. 1994.
Cowley, Good News for Boomers, *Newsweek,* Dec. 30, 1996/Jan. 6, 1997.
Cox, et al., Surgical Treatment of Atrial Fibrillation: A Review, *Europace* (2004) 5, S20-S-29.
Crowley, Electrical Breakdown of Biomolecular Lipid Membranes as an Electromechanical Instability, *Biophysical Journal,* vol. 13, pp. 711-724, 1973.
Davalos, et al., Tissue Ablation with Irreversible Electroporation, *Annals of Biomedical Engineering,* vol. 33, No. 2, Feb. 2005.
Davalos, et al ., Theoretical Analysis of the Thermal Effects During In Vivo Tissue Electroporation, Bioelectrochemistry, vol. 61, pp. 99-107, 2003.
Davalos, et al., A Feasibility Study for Electrical Impedance Tomography as a Means to Monitor T issue Electroporation for Molecular Medicine, *IEEE Transactions on Biomedical Engineering,* vol. 49, No. 4, Apr. 2002.
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.
Dean, Nonviral Gene Transfer to Skeletal, Smooth, and Cardiac Muscle in Living Animals, *Am J. Physiol Cell Physiol* 289: 233-245, 2005.
Dev, et al., Sustained Local Delivery of Heparin to the Rabbit Arterial Wall with an Electroporation Catheter, *Catheterization and Cardiovascular Diagnosis,* Nov. 1998, vol. 45, No. 3, pp. 337-343.
Dev, et al., Medical Applications of Electroporation, *IEEE Transactions of Plasma Science,* vol. 28, No. 1, pp. 206-223, Feb. 2000.
Duraiswami, et al., Boundary Element Techniques for Efficient 2-D and 3-D Electrical Impedance Tomography, *Chemical Engineering Science,* vol. 52, No. 13, pp. 2185-2196, 1997.
Duraiswami, et al., Efficient 2D and 3D Electrical Impedance Tomography Using Dual Reciprocity Boundary Element Techniques, *Engineering Analysis with Boundary Elements* 22, (1998) 13-31.
Duraiswami, et al., Solution of Electrical Impedance Tomography Equations Using Boundary Element Methods, *Boundary Element Technology* XII, 1997, pp. 226-237.
Edd, J., et al., In-Vivo Results of a New Focal Tissue Ablation Technique: Irreversible Electroporaton, *IEEE Trans. Biomed. Eng.* 53 (2006) p. 1409-1415.
Erez, et al., Controlled Destruction and Temperature Distributions in Biological Tissues Subjected to Monoactive Electrocoagulation, *Transactions of the ASME: Journal of Mechanical Design,* vol. 102, Feb. 1980.
Foster, R.S., et al., High-intensity focused ultrasound in the treatment of prostatic disease. *Eur. Urol.,* 1993. 23: 44-7).
Fox, et al., Sampling Conductivity Images via MCMC, Mathematics Department, Auckland University, New Zealand, May 1997.
Gauger, et al., A Study of Dielectric Membrane Breakdown in the Fucus Egg, *J. Membrane Biol.,* vol. 48, No. 3, pp. 249-264, 1979.
Gehl, et al., In Vivo Electroporation of Skeletal Muscle: Threshold, Efficacy and Relation to Electric Field Distribution, *Biochimica et Biphysica Acta* 1428, 1999, pp. 233-240.
Gençer, et al., Electrical Impedance Tomography: Induced-Current Imaging Achieved with a Multiple Coil System, *IEEE Transactions on Biomedical Engineering,* vol. 43, No. 2, Feb. 1996.
Gilbert, et al., Novel Electrode Designs for Electrochemotherapy, *Biochimica et Biophysica Acta* 1334, 1997, pp. 9-14.
Gilbert, et al., The Use of Ultrasound Imaging for Monitoring Cryosurgery, Proceedings 6th Annual Conference, IEEE Engineering in Medicine and Biology, 107-111, 1984.
Glidewell, et al., The Use of Magnetic Resonance Imaging Data and the Inclusion of Anisotropic Regions in Electrical Impedance Tomography, *Biomed, Sci. Instrum.* 1993; 29: 251-7.
Gothelf, et al., Electrochemotherapy: Results of Cancer Treatment Using Enhanced Delivery of Bleomycin by Electroporation, *Cancer Treatment Reviews* 2003: 29: 371-387.
Griffiths, et al., A Dual-Frequency Electrical Impedance Tomography System, *Phys. Med. Biol.,* 1989, vol. 34, No. 10, pp. 1465-1476.
Griffiths, The Importance of Phase Measurement in Electrical Impedance Tomography, *Phys. Med. Biol.,* 1987, vol. 32, No. 11, pp. 1435-1444.
Griffiths, Tissue Spectroscopy with Electrical Impedance Tomography: Computer Simulations, *IEEE Transactions on Biomedical Engineering,* vol. 42, No. 9, Sep. 1995.
Gumerov, et al., The Dipole Approximation Method and Its Coupling with the Regular Boundary Element Method for Efficient Electrical Impedance Tomography, *Boundary Element Technology* XIII, 1999.
Hapala, Breaking the Barrier: Methods for Reversible Permeabilization of Cellular Membranes, *Critical Reviews in Biotechnology,* 17(2): 105-122, 1997.
Heller, et al., Clinical Applications of Electrochemotherapy, *Advanced Drug Delivery Reviews,* vol. 35, pp. 119-129, 1999.
Ho, et al., Electroporation of Cell Membranes: A Review, *Critical Reviews in Biotechnology,* 16(4): 349-362, 1996.
Holder, et al., Assessment and Calibration of a Low-Frequency System for Electrical Impedance Tomography (EIT), Optimized for Use in Imaging Brain Function in Ambulant Human Subjects, *Annals of the New York Academy of Science,* vol. 873, Issue 1, Electrical BI, pp. 512-519, 1999.
Huang, et al., Micro-Electroporation: Improving the Efficiency and Understanding of Electrical Permeabilization of Cells, *Biomedical Microdevices,* vol. 2, pp. 145-150, 1999.
Hughes, et al., An Analysis of Studies Comparing Electrical Impedance Tomography with X-Ray Videofluoroscopy in the Assessment of Swallowing, *Physiol. Meas.* 15, 1994, pp. A199-A209.
Issa, et al., The TUNA Procedure for BPH: Review of the Technology: The TUNA Procedure for BPH: Basic Procedure and Clinical Results, Reprinted from *Infections in Urology,* Jul./Aug. 1998 and Sep./Oct. 1998.
Ivanuša, et al., MRI Macromolecular Contrast Agents as Indicators of Changed Tumor Blood Flow, *Radiol. Oncol.* 2001; 35(2): 139-47.
Jaroszeski, et al., In Vivo Gene Delivery by Electroporation, *Advanced Drug Delivery Review,* vol. 35, pp. 131-137, 1999.
Kinosita, et al., Hemolysis of Human Erythrocytes by a Transient Electric Field, *Proc. Natl. Acad. Sci. USA,* vol. 74, No. 5, pp. 1923-1927, 1977.
Liu, et al., Measurement of Pharyngeal Transit Time by Electrical Impedance Tomography, *Clin. Phys. Physiol. Meas.,* 1992, vol. 13, Suppl. A, pp. 197-200.
Lundqvist, et al., Altering the Biochemical State of Individual Cultured Cells and Organelles with Ultramicroelectrodes, *Proc. Natl. Acad. Sci. USA,* vol. 95, pp. 10356-10360, Sep. 1998.
Lurquin, Gene Transfer by Electroporation, *Molecular Biotechnology,* vol. 7, 1997.
Lynn, et al., A New Method for the Generation and Use of Focused Ultrasound in Experimental Biology, *The Journal of General Physiology,* vol. 26, 179-193, 1942.

Miklavčič, et al., A Validated Model of an in Vivo Electric Field Distribution in Tissues for Electrochemotherapy and for DNA Electrotransfer for Gene Therapy, *Biochimica et Biophysica Acta* 1523 (2000), pp. 73-83.
Miklavčič, et al., The Importance of Electric Field Distribution for Effective in Vivo Electroporation of Tissues, *Biophysical Journal,* vol. 74, May 1998, pp. 2152-2158.
Miller, L., et al., Cancer cells ablation with irreversible electroporation, *Technology in Cancer Research and Treatment* 4 (2005) 699-706.
Mir, Therapeutic Perspectives of In Vivo Cell Electropermeabilization, *Bioelectrochemistry,* vol. 53, pp. 1-10, 2000.
Mir, L.M., et al., Electric Pulse-Mediated Gene Delivery to Various Animal Tissues, in Advances in Genetics, Academic Press, 2005, p. 83-114.
Mir, L.M. And Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Mir, et al., Effective Treatment of Cutaneous and Subcutaneous Malignant Tumours by Electrochemotherapy, *British Journal of Cancer,* vol. 77, No. 12, pp. 2336-2342, 1998.
Mir, et al., Electrochemotherapy Potentiation of Antitumour Effect of Bleomycin by Local Electric Pulses, *European Journal of Cancer,* vol. 27, No. 1, pp. 68-72, 1991.
Mir, et al., Electrochemotherapy, a Novel Antitumor Treatment: First Clinical Trial, *C.R. Acad. Sci. Paris, Ser.* III, vol. 313, pp. 613-618, 1991.
Narayan, et al., Establishment and Characterization of a Human Primary Prostatic Adenocarcinoma Cell Line (ND-1), *The Journal of Urology,* vol. 148, 1600-1604, Nov. 1992.
Naslund, Michael J., Transurethral Needle Ablation of the Prostate, *Urology,* vol. 50, No. 2, Aug. 1997.
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.
Neumann, et al., Gene Transfer into Mouse Lyoma Cells by Electroporation in High Electric Fields, *J. Embo.,* vol. 1, No. 7, pp. 841-845, 1982.
Neumann, et al., Permeability Changes Induced by Electric Impulses in Vesicular Membranes, *J. Membrane Biol.,* vol. 10, pp. 279-290, 1972.
Okino, et al., Effects of High-Voltage Electrical Impulse and an Anticancer Drug on In Vivo Growing Tumors, *Japanese Journal of Cancer Research,* vol. 78, pp. 1319-1321, 1987.
Onik, et al., Sonographic Monitoring of Hepatic Cryosurgery in an Experimental Animal Model, *AJR American J. of Roentgenology,* vol. 144, pp. 1043-1047, May 1985.
Onik, et al., Ultrasonic Characteristics of Frozen Liver, *Cryobiology,* vol. 21, pp. 321-328, 1984.
Organ, L.W., Electrophysiological principles of radiofrequency lesion making, *Apply. Neurophysiol.,* 1976. 39: p. 69-76.
Piñero, et al., Apoptotic and Necrotic Cell Death Are Both Induced by Electroporation in HL60 Human Promyeloid Leukaemia Cells, *Apoptosis,* vol, 2, No. 3, 330-336, Aug. 1997.
Precision Office TUNA System, When Patient Satisfaction is Your Goal.
Rols, M.P., et al., Highly Efficient Transfection of Mammalian Cells by Electric Field Pulses: Application to Large Volumes of Cell Culture by Using a Flow System, *Eur. J. Biochem.* 1992, 206, pp. 115-121.
Rubinsky, B., ed, Cryosurgery. *Annu Rev. Biomed.* Eng. vol. 2 2000. 157-187.
Schmukler, Impedance Spectroscopy of Biological Cells, downloaded from IEEE Xplore website.
Sersa, et al., Reduced Blood Flow and Oxygenation in SA-1 Tumours after Electrochemotherapy with Cisplatin, *British Journal of Cancer,* 87, 1047-1054, 2002.
Sersa, et al., Tumour Blood Flow Modifying Effects of Electrochemotherapy: a Potential Vascular Targeted Mechanism, *Radiol. Oncol.,* 37(1): 43-8, 2003.
Sharma, et al., Poloxamer 188 Decreases Susceptibility of Artificial Lipid Membranes to Electroporation, *Biophysical Journal,* vol. 71, No. 6, pp. 3229-3241, Dec. 1996.
Shiina, S., et al, Percutaneous ethanol injection therapy for hepatocellular carcinoma: results in 146 patients. AJR, 1993, 160: p. 1023-8.
Thompson, et al., To determine whether the temperature of 2% lignocaine gel affects the initial discomfort which may be associated with its instillation into the male urethra, *BJU International* (1999), 84, 1035-1037.
TUNA—Suggested Local Anesthesia Guidelines.
Vidamed, Inc., Transurethral Needle Ablation (TUNA): Highlights from Worldwide Clinical Studies, Vidamed's Office TUNA System.
Weaver, Electroporation: A General Phenomenon for Manipulating Cells and Tissues, *Journal of Cellular Biochemistry,* 51: 426-435, 1993.
Weaver, et al., Theory of Electroporation: A Review, *Bioelectrochemistry and Bioenergetics,* vol. 41, pp. 136-160, 1996.
Zimmermann, et al., Dielectric Breakdown of Cell Membranes, *Biophysical Journal,* vol. 14, No. 11, pp. 881-899, 1974.
Zlotta, et al., Possible Mechanisms of Action of Transurethral Needle Ablation of the Prostate on Benign Prostatic Hyperplasia Symptoms: a Neurohistochemical Study, Reprinted from *Journal of Urology,* vol. 157, No. 3, Mar. 1997, pp. 894-899.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

* cited by examiner

APPARATUS AND METHOD FOR REDUCING SUBCUTANEOUS FAT DEPOSITS BY ELECTROPORATION

Matter enclosed in heavy brackets [ ] appears in the original patent but forms no part of this reissue specification; matter printed in italics indicates the additions made by reissue.

*CROSS-REFERENCE TO RELATED APPLICATIONS*

The present application claims priority from and is a continuation-in-part of U.S. patent application Ser. No. 09/931,672, filed Aug. 17, 2001, entitled Apparatus and Method for Reducing Subcutaneous Fat Deposits, Virtual Face Lift and Body Sculpturing by Electroporation, *now U.S. Pat. No. 6,892,099,* the specification and drawings of which are incorporated herein in their entirety by reference*, which claims the benefit of U.S. Provisinal Application Ser. No. 60/267,106 filed Feb. 8, 2001 and U.S. Provisional Application Ser. No. 60/225,775, filed Aug. 17, 2000*. The present application also claims priority from U.S. Provisional Patent Application Serial No. 60/358,443, filed Feb. 22, 2002, and entitled Apparatus and Method for Reducing Subcutaneous Fat Deposits by Electroporation, the specification and drawings of which are incorporated herein in their entirety by reference.

FIELD OF INVENTION

The present invention relates generally to electroporation in-vivo and specifically to apparatus and method for reducing subcutaneous fat deposits and/or for performing virtual face lifts and/or body sculpturing.

BACKGROUND OF INVENTION

"Cosmetic surgery" is a phrase used to describe broadly surgical changes made to a human body with the usual, though not always, justification of enhancing appearance. This area of medical practice constitutes an ever-growing industry around the world. Obviously, where such a procedure fails to deliver an enhanced appearance, the procedure fails to meet the desired goal. One of the reasons that the majority of current procedures fail to deliver upon their promise is that, for the most part, current procedures are invasive, requiring incisions and suturing, and can have serious and unpleasant side effects, including but not limited to scarring, infection, and loss of sensation.

One of the more common forms of cosmetic surgery is the "face-lift." A face-lift is intended to enhance facial appearance by removing excess facial skin and tightening the remaining skin, thus removing wrinkles. A face-lift is traditionally performed by cutting and removing portions of the skin and underlying tissues on the face and neck. Two incisions are made around the ears and the skin on the face and neck is separated from the subcutaneous tissues. The skin is stretched, excess tissue and skin are removed by cutting with a scissors or scalpel, and the skin is pulled back and sutured around the ears. The tissue tightening occurs after healing of the incisions because less skin covers the same area of the face and neck and also because of the scars formed on the injured areas are contracting during the healing process.

Traditional face-lift procedures are not without potential drawbacks and side effects. One drawback of traditional cosmetic surgery is related to the use of scalpels and scissors. The use of these devices sometimes leads to significant bleeding, nerve damage, possible infection and/or lack of blood supply to some areas on the skin after operation. Discoloration of the skin and alopecia (baldness) are other possible side effects of the standard cosmetic surgery. The overall quality of the results of the surgery is also sometimes disappointing to the patients because of possible over-corrections, leading to undesired changes in the facial expression. Additionally, face-lift procedures require a long recovery period before swelling and bruising subside.

The use of lasers to improve the appearance of the skin has been also developed. Traditional laser resurfacing involves application of laser radiation to the external layer of the skin—the epidermis. Destruction of the epidermis leads to rejuvenation of the epidermis layer. The drawback of the laser resurfacing procedure is possible discoloration of the skin (red face) that can be permanent.

Another laser procedure involves using optical fibers for irradiation of the subcutaneous tissues, such as disclosed in U.S. Pat. No. Re36,903. This procedure is invasive and requires multiple surgical incisions for introduction of the optical fibers under the skin. The fibers deliver pulsed optical radiation that destroys the subcutaneous tissues as the tip of the fiber moves along predetermined lines on the face or neck. Debulking the subcutaneous fat and limited injury to the dermis along the multiple lines of the laser treatment results in contraction of the skin during the healing process, ultimately providing the face lift. The drawback of the method is its high price and possibility of infection.

Electrosurgical devices and methods utilizing high frequency electrical energy to treat a patient's skin, including resurfacing procedures and removal of pigmentation, scars, tattoos and hairs have been developed lately, such as disclosed in U.S. Pat. No. 6,264,652. The principle drawback of this technology is collateral damage to the surrounding and underlying tissues, which can lead to forming scars and skin discoloration.

Other forms of cosmetic surgery are also known. One example is liposuction, which is an invasive procedure that involves inserting a suction device under the skin and removing fat tissues. As with other invasive surgical procedures, there is always a risk of infection. In addition, because of the invasive nature of the procedure, physicians usually try to minimize the number of times the procedure must be performed and thus will remove as much fat tissue as possible during each procedure. Unfortunately, this procedure has resulted in patient deaths when too much tissue was removed. Assuming successful removal of excess fat tissue, further invasive surgery may be required to accomplish desired skin tightening.

The prior art to date, then, does not meet the desired goal of performing cosmetic surgery in a non-invasive manner while causing minimal or no scarring of the exterior surface of the skin and at the same time resulting in the skin tightening.

The term "electroporation" (EP) is used herein to refer to the use of a pulsed electric field to induce microscopic pores in the biological membranes, also commonly called a cell wall, of living cells. The cell membrane separates the inner volume of a cell, or cytosol, from the extracellular space, which is filled with lymph. This membrane performs several important functions, not the least of which is maintaining gradients of concentration of essential metabolic agents across the membrane. This task is performed by active protein transporters, built in the membrane and providing transport of the metabolites via controlled openings in the membrane. Normally, the active protein transporters, or pumps, which routinely provide transport of various metabolic agents, especially proteins, across the cell membrane, use either the energy of positive ions (hydrogen or sodium ions) passing from the positive potential of the intracellular space to the negative potential of the cytosol, or the energy of negative ions (chlorine ions) for movement across the membrane in the opposite direction. This energy supply for the protein transporters is provided by maintaining the potential difference across the membrane, which, in turn, is linked to the difference in concentrations of sodium and potassium ions across the membrane. When this potential difference is too low, thousands of the active transporters find themselves out of power.

Inducing relatively large pores in the cell membrane by electroporation creates the opportunity for a fluid communication through the pores between the cytosol and the extracellular space that may lead to a drastic reduction of these vitally important gradients of concentrations of the metabolic agents and thus a reduction in the potential difference across the membrane. Uncontrolled exchange of metabolic agents, such as ions of sodium, potassium, and calcium between a living cell and the extracellular space imposes on the cell intensive biochemical stress.

When a cell is undergoing biochemical stresses the major biochemical parameters of the cell are out of equilibrium and the cell cannot perform its routine functions. Invasion of very high concentration of calcium ions through membrane pores from the interstitial space between cells, where the calcium ion concentration is about 100 times higher than in the cytosol, can create such stresses by reducing the potential difference across the membrane. In an attempt to repair itself, the cell starts working in a damage control mode: an emergency production of actin filaments is triggered that extend across the large pores in the membrane in an attempt to bridge the edges of the pores, pull the edges together, and thereby seal the membrane. In muscle cells the calcium ion invasion may cause lethal structural damage by forcing the cell to overcontract and rupture itself. Small pores in the membrane created by a relatively short electric pulse can reseal themselves spontaneously and almost instantaneously after the removal of electric field. No significant damage to the cell is done in this case. Contrary to that, larger pores may become meta-stable with very long life time and cause irreversible damage. It can be said that, depending on the number, effective diameter -and life time of pores in the membrane, electroporation of the cell may result in significant metabolic or structural injury of the cell and/or its death. The cause of cell death after electroporation is believed to be an irreversible chemical imbalance and structural damage resulted from the fluid communication of the cytosol and the extracellular environment.

Below a certain limit of the electric field no pores are induced at all. This limit, usually referred to as the "lower EP limit" of electroporation, is different for different cells, depending, in part, on their sizes in an inverse relationship. That is, pores are induced in larger cells with smaller electric fields while smaller cells require larger electric fields. Above the lower EP limit the number of pores and their effective diameter increase with both the amplitude and duration of the electric field pulses.

Removing the electric field pulses enables the induced pores to reseal. This process of resealing of the pores and the ability of the cell to repair itself, discussed briefly above, currently is not well understood. The current understanding is that there is a significant range of electric field amplitudes and pulse durations in which cells survive electroporation and restore their viability thereafter. An electroporated cell may have open pores for as long as many minutes and still survive. The range of electric field amplitudes and pulse durations in which cells survive is successfully used in current biomedical practice for gene transfer and drug delivery inside living cells.

Nevertheless, the survivability of electroporated cells is limited As the electric field amplitude and/or duration of pulses, increases, this limit, usually referred to as the "upper EP limit" of electroporation, is inevitably achieved. Above the upper EP limit, the number and sizes of pores in the cellular membrane become too large for a cell to survive. Multiple pulses cause approximately the same effect on the cells as one pulse with a duration equal to the total duration of all applied pulses. After application of an electrical pulse above the upper electroporation limit the cell cannot repair itself by any spontaneous or biological process and dies. The upper EP limit is defined by the combinations of the amplitudes of electric field and pulse durations that cause cellular death.

The vulnerability of cells to electroporation depends on their size: the larger the cell, the lower the electric field and duration of a pulse capable of killing it. If cells of different sizes are exposed to the same electric field, the largest cells will die first. Thus, this ability of electroporation to discriminate cells by their sizes may be used to selectively kill large cells in the human body.

In the previously referred to application for U.S. patent application entitled "Apparatus and Method for Reducing Subcutaneous Fat Deposits, Virtual Face Lift and Body Sculpting by Electroporation", Ser. No. 09/931,672, filed Aug. 17, 2001, an apparatus and method for performing non-invasive treatment of the human face and body by electroporation in lieu of cosmetic surgery is disclosed. The apparatus comprises a high voltage pulse generator and an applicator having two or more electrodes utilized in close mechanical and electrical proximity with the patient's skin to apply electrical pulses thereto. The applicator may include at least two electrodes with one electrode having a sharp tip and another having a flat surface. High voltage pulses delivered to the electrodes create at the tip of the sharp electrode an electric field high enough to cause death of relatively large subcutaneous fat cells by electroporation. Moving the electrode tip along the skin creates a line of dead subcutaneous fat cells, which later are metabolized by the body. Multiple applications of the electrode along predetermined lines on the face or neck create shrinkage of the skin and the subcutaneous fat reduction under the treated area.

The electroporation in-vivo, employed in the disclosed method is a non-invasive treatment of subcutaneous fat, which, as was previously described before, involves application of high amplitude electric pulses between external electrodes to cause death by electroporation of the subcutaneous fat cells. Fat cells, being typically larger than other cells of the body, are more easily killed by electroporation treatment than are smaller lean muscle cells. The electric field, applied to the external electrodes, is efficient for cell killing in the subcutaneous layer of fat tissue directly under the skin. However, the amplitude of the field significantly decreases with increasing the depth of the deposits of fat cells. The deeper penetration of the electric field may be achieved by increasing the distance between electrodes with simultaneous increase in the operating voltage. This approach, though, leads to concomitant increase of the volume that is treated by electroporation. Occasionally, during such cosmetic and body sculpting procedures as described above, a small volume of deep subcutaneous fat deposit must be treated. The non-invasive method of treating subcutaneous tissue by electroporation as described in the earlier referenced patent application, in which the high voltage pulses are applied to the external electrodes, is sometimes difficult to apply to deep fat deposits especially when a fine spatial resolution is required It would be desirable to have available an apparatus and a method for electroporation treatment to reduce deep fat deposits by allowing deep localized application of the electroporation pulses that can provide high spatial resolution of the body sculpting. Preferably, such apparatus and methods would also be minimally invasive.

SUMMARY OF THE INVENTION

The present invention provides an apparatus and method for creation of a controlled electroporation injury to deep subcutaneous fat tissues that, with the healing that follows, leads to permanent loss of the fat cells in the treated tissue. According to present invention an electric field capable of killing fat cells in deep subcutaneous deposits may be applied by a set of needle electrodes, configured for placement deeply under the skin. An apparatus according to the current invention comprises a voltage pulse generator, an applicator with two or multiple electrodes of different shapes and sizes, and a cable connecting the electrodes to the pulse generator. The pulse generator produces a sequence of high voltage pulses of predetermined amplitude, duration and number to cause necrosis in a treated area of the subcutaneous tissue.

A method of weight loss and body sculpturing in accord with the present invention comprises application of electrical pulses to the electrodes positioned under the skin in a treatment area of the subcutaneous fat tissue. The amplitude, duration and number of applied pulses are selected to cause necrosis of fat cells at a predetermined distance around the needles in the subcutaneous tissue. During the treatment a number of sites in a predetermined pattern are exposed to electroporation. Later, during the healing process the treated area contracts as the electroporated cells die and are metabolized by the body, thus reducing volume of fat tissue and providing desired change of body contours. The injury to the tissues made by electroporation is very selective, targeting only large fat cell and not damaging the epidermis, the most external layer of the skin. As a matter of fact, in accordance with the current invention, the electrical field is applied only to the deep subcutaneous fat deposits, no electric field is applied to the skin of the patient.

The present invention, as well as its various features and advantages, will become evident to those skilled in the art when the following description of the invention is read in conjunction with the accompanying drawings as briefly described below and the appended claims. Throughout the drawings, like numerals refer to similar or identical parts.

DESCRIPTION OF THE DRAWINGS

FIG. 2 shows time diagrams for high voltage pulses during EP treatment wherein

DESCRIPTION OF THE INVENTION

Figure 1:
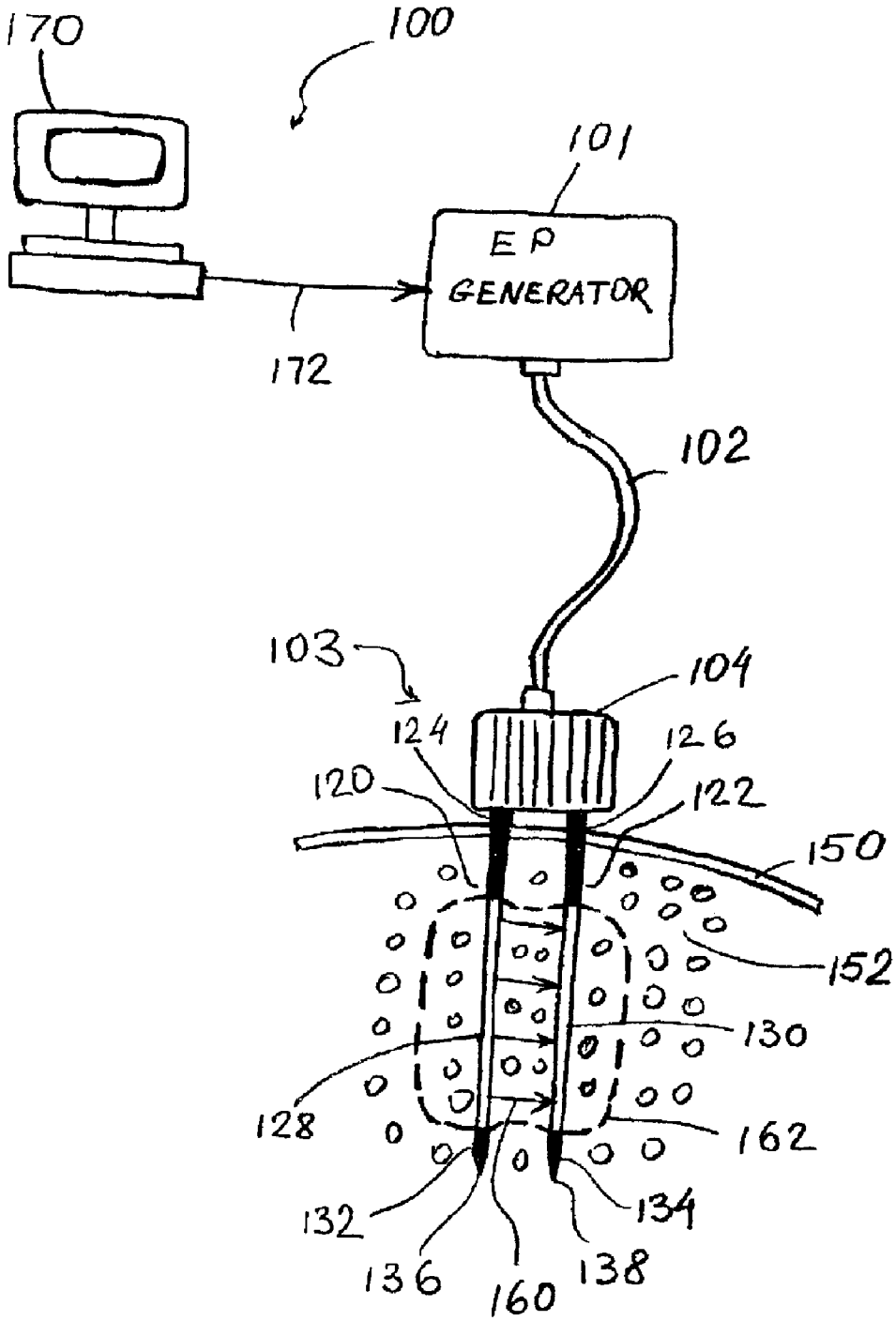
FIG. 1 is a schematic illustration of an electroporation system for treatment of deep subcutaneous fat deposits.

FIG. 1 shows schematically an electroporation system 100 for in-vivo treatment of deep subcutaneous fat deposits. The system 100 includes a high voltage electroporation pulse generator 101 connected by an appropriate connector 102 to an applicator 103. Applicator 103 may include a handle 104 and a pair of needle 120 and 122 extending therefrom. Handle 104 may be used by the operator for the safe and efficacious placement of the needles 120 and 122 in a selected-for-treatment anatomical site. Needles 120 and 122 may include proximal insulated portions 124 and 126, respectively, central uninsulated portions 128 and 130, respectively, and distal insulated portions 132 and 134. Preferably, distal portions 132 and 134 includes sharpened ends or tips 136 and 138, respectively.

As illustrated in the Figure, an operator of system 100 will use handle 104 to push the tips 136 and 138 through the skin 150 of the patient into a deep subcutaneous fat deposit 152. The sharpened tips 136 and 138 facilitate penetration of the skin 150 and fat tissue 152 while minimizing pain or serious discomfort to the patient. Insulated proximal portions 124 and 126 of needles 120 and 122, respectively, provide electrical insulation from the skin 150 during an EP treatment. That is, this insulation prevents a current flow from the needles 120 and 122 through the skin and with it an associated discomfort of the patient. Similarly, the insulated distal portions 132 and 134 of needles 120 and 122 helps to avoid spark discharges between the tips during high voltage electroporation pulsing.

Central portions 128 and 130 form the electrodes for the system 10, which as noted are uninsulated. The electrodes 128 and 130 are in close electrical contact with the surrounding tissue 152 and provide a pulsed electrical field, as indicated by shown by arrows 160, to the treatment zone 162 between and around electrodes 128 and 130, as indicated by dotted line 162. It will be understood that the treatment zone is actually a three dimensional zone extending in all directions from the electrodes 128 and 130.

The larger the diameter of the cells or the higher applied voltage, the larger treatment zone 162 will be where the cells are actually killed. It should be mentioned that not all cells die at any point of the treatment zone. The smaller fat cells will survive. As was mentioned early, cell killing by electroporation is selective on the cell size and the upper EP limit is higher for small cells. Small fat cells, for which applied electric field is below the upper electroporation limit, will survive any reasonable number of electric pulses without any morphological or functional damage and will stay in the tissue. Also, there is no electroporation treatment for the tissues interfacing the insulated parts of the needles.

A computer 170 connected by an appropriate connector 172 to EP generator 101, may be provided to control the whole procedure of EP treatment: the predetermined amplitude, duration, and number of EP pulses supplied to the electrodes 128 and 130. The EP pulses may be applied with a repetition rate of about 1 to about 50 Hz and may have a current peak of about 0.5 to about 10 A depending on the size and shape of electrodes. Generally, the voltage of the EP pulses can be in the range of about 50 V to about 5000 V with a duration from about 10 microseconds to about 10.0 milliseconds depending on the location of the treated segment of the body, the sizes and shapes of the electrodes, and the distance between the electrodes. Regardless of the possible configuration of the electrodes and the voltages applied to the treatment volume, the voltage applied to an individual subcutaneous fat cell should fall in the range of about 2 to about 10 V per cell to be able to kill it.

To achieve successful cell killing by electroporation the electric field applied to the treated volume of cells must be above the upper EP limit for the cells. The probability of cell killing increases if longer or multiple pulses are employed.

According to present invention high voltage pulses of different waveforms may be used for the EP treatment. The pulses may be rectangular or exponential in shape, be unipolar (positive or negative only) or bipolar (positive and negative). Bipolar rectangular pulses are known to be very efficient in cell killing by electroporation. This is because both directions of the electrical field, positive and negative, are equally efficient in creating pores in cellular membranes, and the electric field strength, contrary to the exponential pulses, stays high during the whole pulse. The efficiency results because electroporation is a process related to the difference in the energy of the porous and non-porous membrane in the presence of an electric field. The energy difference depends on the square of the amplitude (or strength) of the electric field (i.e., $E^2$) and does not depend on the sign or polarity (+ or −) of the electric field.

From a practical stand point, however, applying balanced pulses during in-vivo electroporation treatment has one important advantage. Contrary to unipolar pulsing, that carries a direct current component into the treated tissue and creates undesired electrolytic effects on the interface of the electrodes and tissues, bipolar pulsing is free from these drawbacks. With bipolar pulsing of the field, problems such as metal depositions from the electrodes or chemical decomposition of tissue during treatment are largely if not completely avoided.

These advantageous properties of balanced pulses, namely, high efficiency in cell killing and freedom from electrolytic effects, make using rectangular bipolar balanced pulses a preferred mode for electroporation pulsing in the current invention. Technically, balancing of two pulses of the opposite polarities may be easily achieved by using a pulse generator having a direct current blocking capacitor electrically coupled in series to the needle electrodes.

Figure 2A:
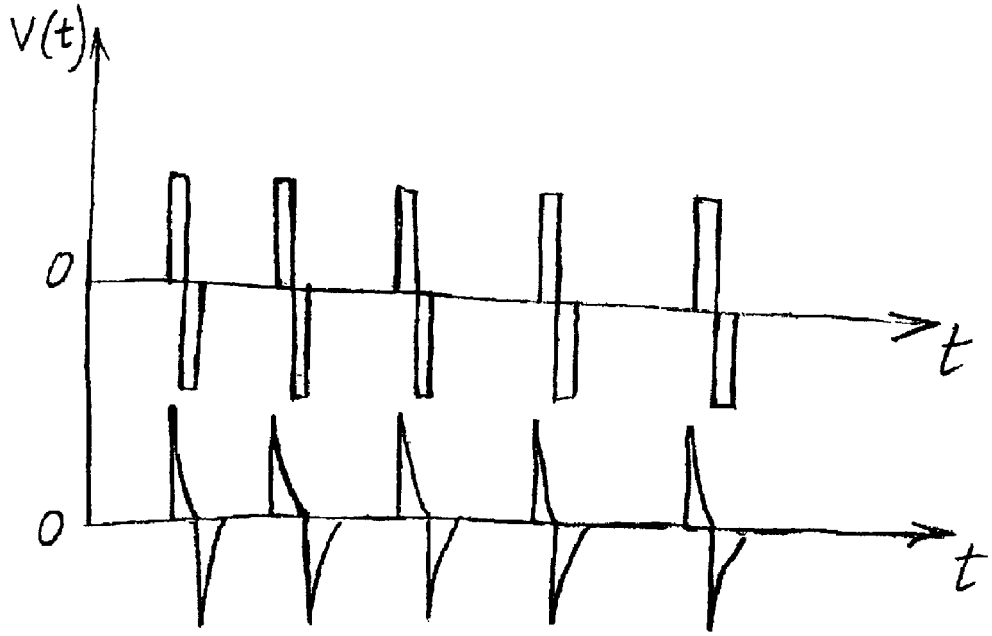
FIG. 2a illustrates unipolar pulsing and FIG. 2b illustrates bipolar pulsing.
Figure 2B:
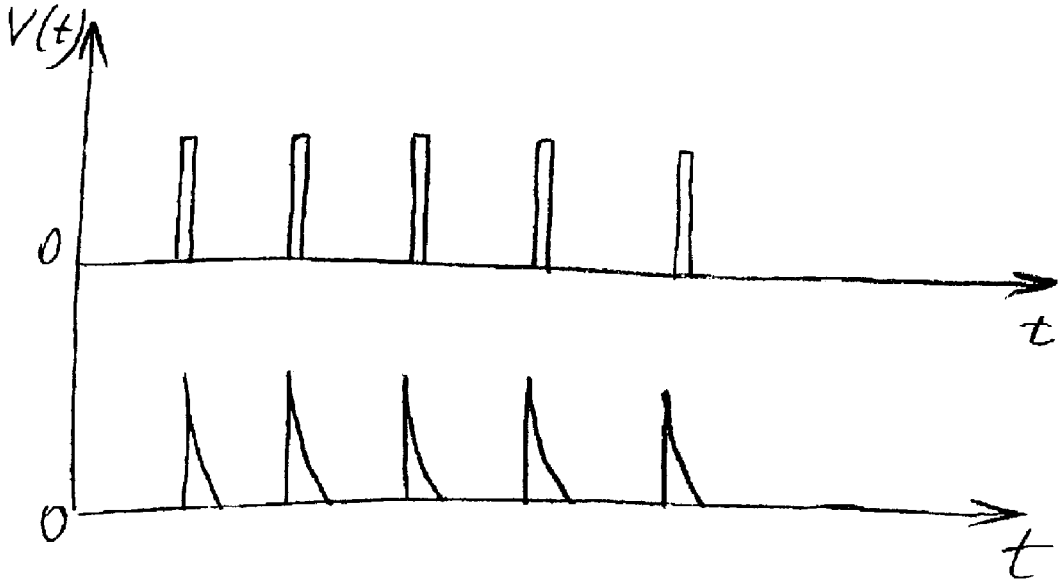

In FIGS. 2a and 2b plots of high voltage EP pulses against time are shown. In FIG. 2a the upper curve shows a plot of rectangular balanced pulses, the preferred embodiment and the lower curve shows exponential balanced pulses. FIG. 2b depicts rectangular and exponential unipolar pulses in the upper and lower curves, respectively.

Figure 3:
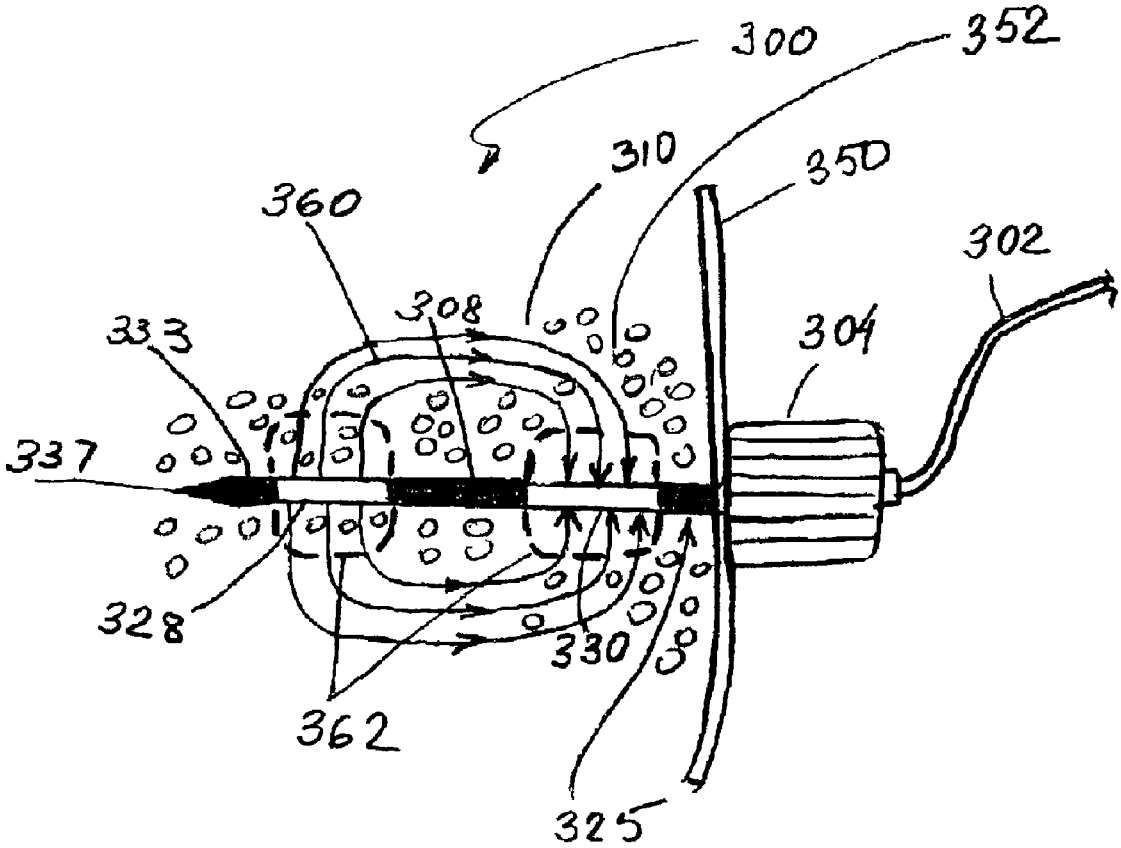
FIG. 3 illustrates a one-needle applicator with two electrodes.

In FIG. 3 another embodiment 300 of the needle applicator is shown. Needle applicator 300 comprises a single needle 310 with two axially separated electrodes 328 and 330 of opposite polarity insulated from each other and separated by insulator 308. The needle may be made of a hollow tube carrying inside two conductors connecting electrodes 328 and 330 via cable 302 to the output of the EP generator, not shown in the figure. Proximal end 325 of the needle 310 is covered with an insulation layer to protect the skin of the patient during treatment from an electric current and discomfort associated with it. To avoid sparking from the distal end 333 of the applicator the needle 310 may be made of insulating material or of a metal piece electrically insulated from the electrodes 328 and 330. Additionally, distal end 333 may have a sharp tip 337.

The electric field between electrodes 328 and 330 is shown by lines 360. Dotted lines 362 delineate the treatment zone, where the electric field is the highest and where actual killing cells by electroporation occurs.

Figure 4A:
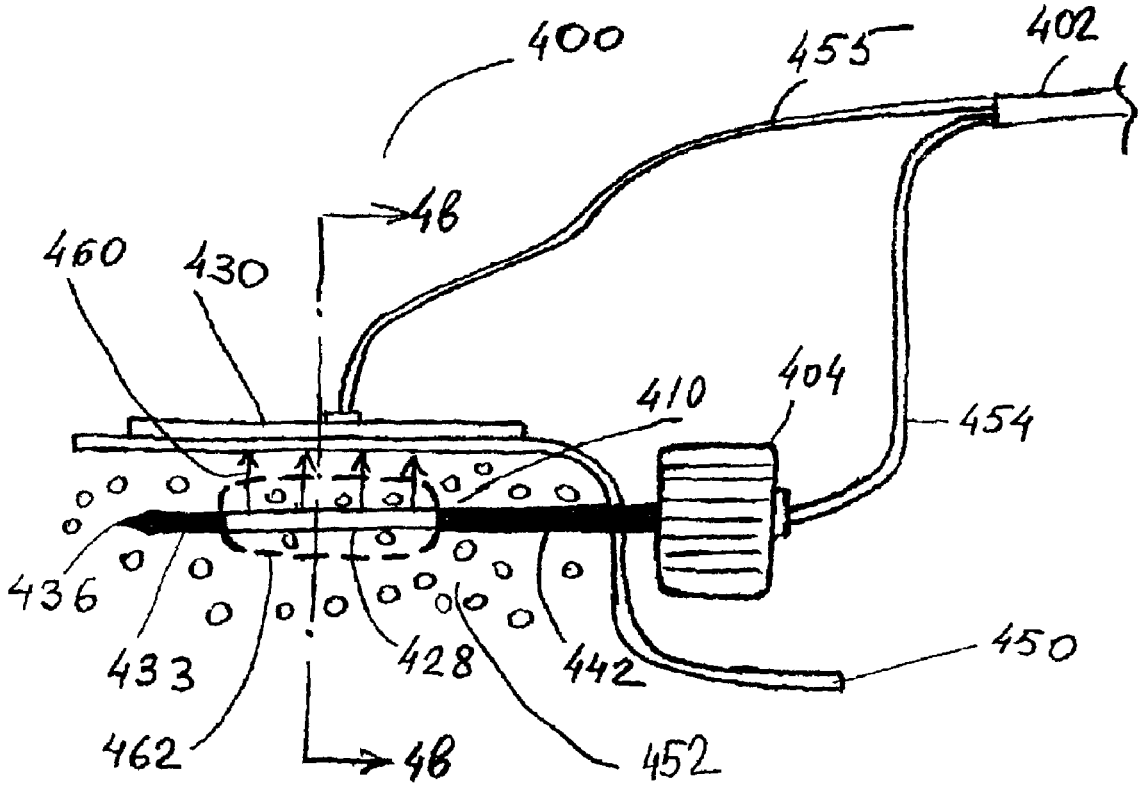
FIG. 4 illustrates an embodiment of an applicator comprising one needle in combination with an external patch electrode wherein FIG. 4a provides a plan view and FIG. 4b provides a cross-sectional view taken along viewing plane 4b—4b.
Figure 4B:
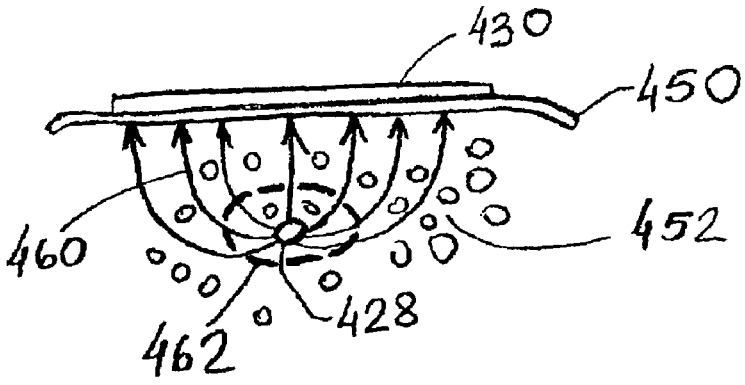

Yet another embodiment 400 of the needle applicator is shown in FIG. 4 in two substantially orthogonal views, namely FIGS. 4a and 4b. Applicator 400 comprises a needle 410 with an electrode 428 combined with a patch electrode 430. Patch electrode 430 is placed on the skin 450 of the patient near the treatment site, which is delineated by a dotted line 462. Needle 410 may include a sharp tip 436 and insulated proximal and distal portions 442 and 433 on either side of electrode portion 428 of needle 410. The electrical field lines generated between electrodes 428 and 430 are indicated by lines 460. High voltage EP pulses during treatment are delivered to the electrodes 428 and 430 via appropriate conductors 454 and 455, respectively, which are connected to the connector 402 coupled to the output of the EP generator 101, not shown in the FIG. 4.

During use of the needle applicator 400, the electroporation leading to cellular death occurs only around the conductive surface, i.e., electrode 428, of the needle placed in the tissue. No electroporation takes place near the patch electrode 430 on the skin because the value of the electric field near its surface is less than the upper EP limit. FIG. 4b shows cross section of the applicator. Dotted line 462 delineates the treatment zone around the electrode 428 where the fat cells are killed.

Figure 5:
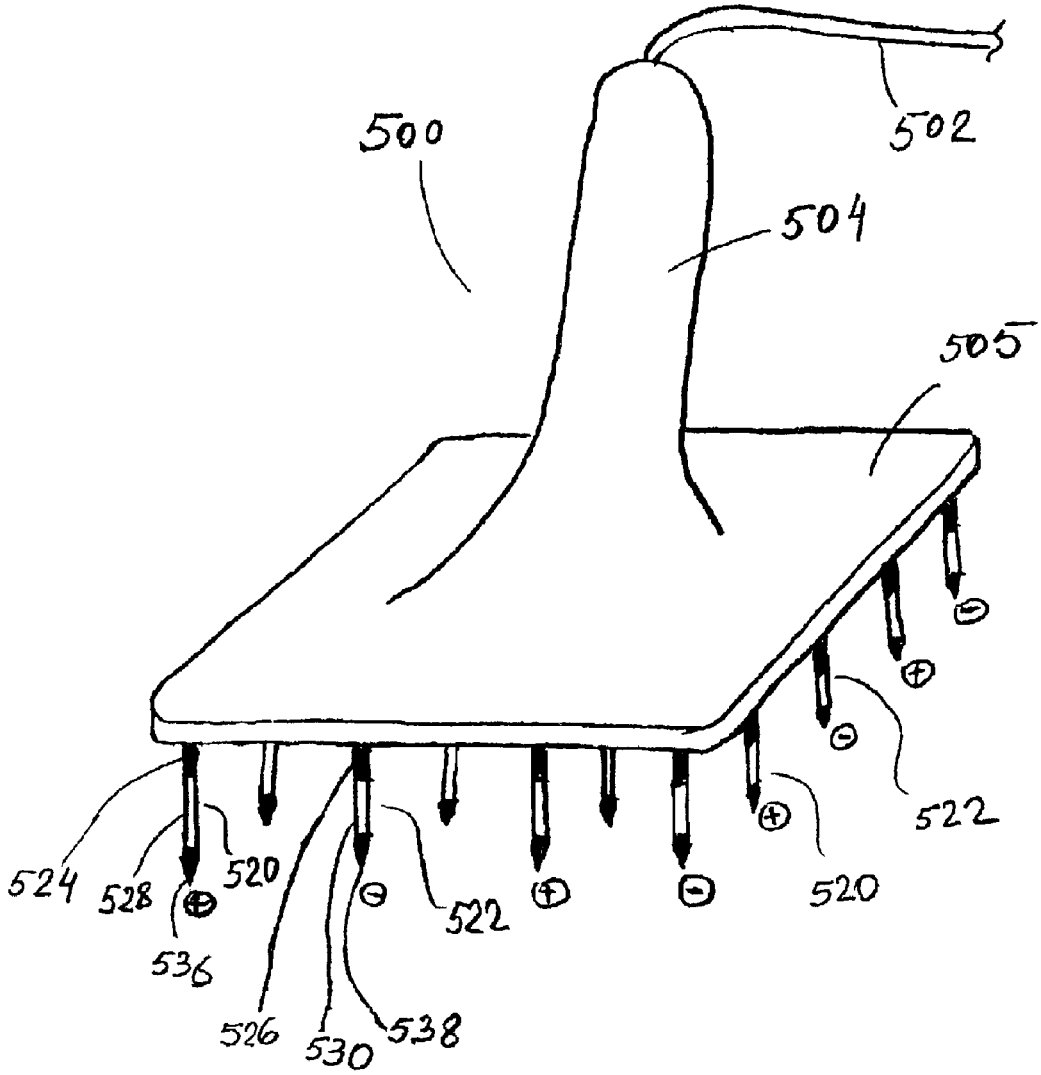
FIG. 5 illustrates an embodiment of the applicator comprising an array of needle electrodes.

FIG. 5 shows yet another implementation 500 of a needle applicator in accord with the present invention. Applicator 500 comprises a handle 504 supporting a needle frame 505. Needle frame 505 supports a plurality of needles 520 of one polarity (positive) and a plurality of needles 522 including an electrode of the other polarity (negative), with each needle of one polarity being adjacent to one or more needles of the other polarity. Handle 504 is connected via connector 502 to the output of the EP generator 101 (not shown in the Figure). The needles 520 and 522 in the needle array alternately have positive and negative polarity. The needles 520 and 522 may include a proximal insulated portion 524 and 526, central electrode portions 528 and 530, and distal insulated portions 536 and 538 respectively. Each needle 520 and 522 will also preferably include sharp tip 536 and 538. For EP treatment of subcutaneous deposits the needles are placed preferably normally to the skin. One of benefits of this configuration is that the tissue electroporation occurs in thin cylindrical layers around the electrodes and later, during healing process, macrophages from nearby blood vessels will travel a shorter distance to the damaged cells. Thus, this configuration may accelerate the disposal of the dead fat cells.

Figure 6A:
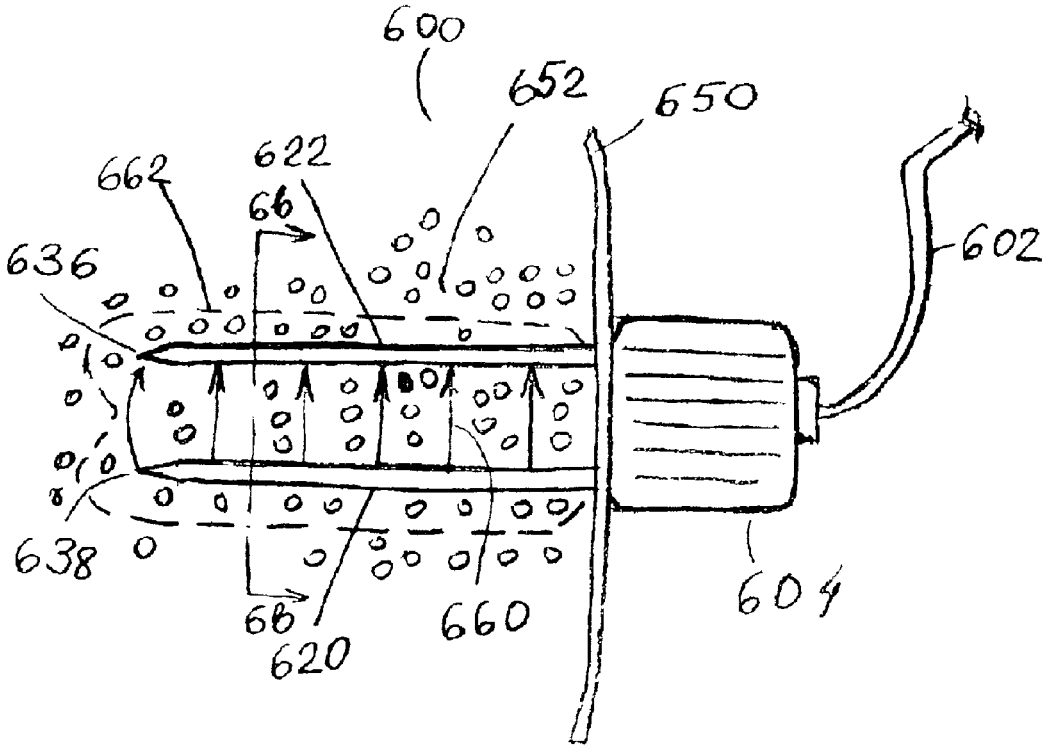
FIG. 6 illustrates in orthogonal views in FIGS. 6a and 6b an embodiment of the applicator comprising needle electrodes without insulated parts.
Figure 6B:
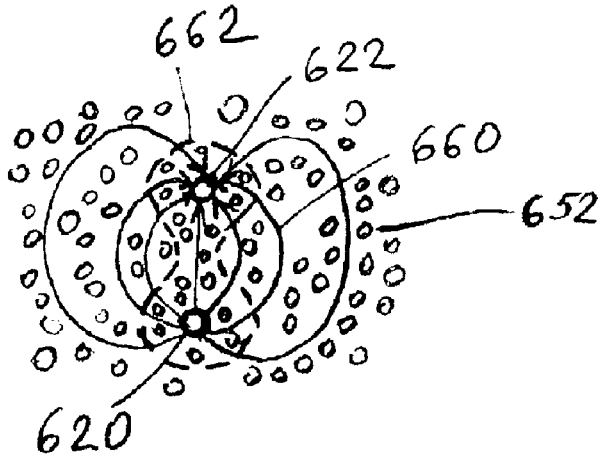

Yet another implementation of the needle applicator is shown in FIG. 6. Applicator 600 may include a handle 604 and a pair of needle 620 and 622 extending therefrom. Handle 604 may be used by the operator for the safe and efficacious placement of the needles 620 and 622 in a selected-for-treatment anatomical site. The sharpened tips 636 and 638 facilitate penetration of the skin 650 and fat tissue 652 while minimizing pain or serious discomfort to the patient. In this implementation of the current invention the whole needles 620 and 622 perform function of electrodes; that is, the needles 620 and 622 do not include insulated portions as in the previously described embodiments. Via an appropriate connector 602 needles 620 and 622 are connected to the EP generator (not shown in the Figures) providing high voltage pulses during treatment. Electric field lines between electrodes 620 and 622 are shown by arrows 660. Dotted line 662 shows the treatment area of the fat tissue 652 where electroporation actually kills fat cells.

Needle electrode diameters may fall in a range of about 0.3 mm to about 1.0 mm, which corresponds to the standard of minimally invasive size. The distance between adjacent needles may be in a range of several mm to several cm. Applied voltage, depending on the distance between needles and the size of the fat cells to be killed, may vary in a wide range from about 100 V to several hundreds and even thousands of volts. In any case the resultant electric field applied to the treated fat cells must be above their upper electroporation limit, or about 2 to about 10 V per cell. The electroporation pulses during treatment may be applied simultaneously to all electrodes or in a sequence of sets of two to several electrodes throughout the whole treated area. The number of pulses per treatment of a selected site may vary from several pulses to several tens of pulses. Preferred duration of the pulses is from about 10 microseconds to about 10 milliseconds.

A method for electroporation treatment of deep subcutaneous fat deposits comprises providing a high voltage pulse generator for generation EP pulses and a needle applicator. The needle applicator or needle applicator and pad electrode may be placed by a physician in an anatomically selected site of treatment under ultrasound or other type of imaging guidance. After the needle placement a sequence of high voltage EP pulses is applied to the electrodes. The electrodes may be placed in plurality of treatment sites in accordance with a treatment plan developed by a physician. Sequences of the high voltage EP pulses are repeatedly applied to the electrodes. After a session of electroporation treatment the remnants of fat cells and released lips will be metabolized and removed by the patient's body over about a two week period. A subsequent electroporation treatment can then be performed with new treatment sites selected for the electroporation treatment. In this manner, then, a patient's body can be sculpted as desired.

The present invention has been described in language more or less specific as to the apparatus and method features. It is to be understood, however, that the present invention is not limited to the specific features described, since the apparatus and method herein disclosed comprise exemplary forms of putting the present invention into effect. For example, while the needles have been described as having sharp tips, blunted end needles may also be used. Additionally, as indicated in the Figures, insulation may be used on the needles in some embodiments, but not others. The invention is, therefore, claimed in any of its forms or modifications within the proper scope of the appended claims appropriately interpreted in accordance with the doctrine of equivalency and other applicable judicial doctrines.

What is claimed is:

1. An apparatus for reducing subcutaneous fat deposits by electroporation comprising:

an applicator comprising a plurality of needle electrodes adapted for penetrating the skin of a patient and applying a high amplitude pulsed electric field to the area of the subcutaneous volume of fat tissue to be treated by electroporation, at least one of said plurality of needle electrodes includes insulated portions and a pair of uninsulated needle portions axially separated along said needle electrode, wherein said uninsulated needle portions form axially separate electrodes of opposite polarity; and said insulated portions include proximal, distal, and central insulated portions, said proximal insulated portion being provided for insulating the skin of the patient during an electroporation treatment, said distal insulated portion being provided to avoid spark discharges to an adjacent needle electrode and said central insulated portion separating said electrodes, wherein said electrodes are disposed on said needle electrode such that they are disposed within the subcutaneous fat deposit during treatment;

a generator of high voltage pulses for applying pulsed electric field to the electrodes, said pulses generating an electric field above the upper electroporation limit for subcutaneous fat cells in the volume of subcutaneous fat tissue to be treated; and connectors connecting said generator of high voltage electrical pulses with corresponding needle electrodes placed under the skin.

2. An apparatus according to claim 1 wherein said high voltage pulses have a duration in a range of about 10 microseconds to about 10 millisecond.

3. An apparatus according to claim 1 wherein the amplitude of the electric field applied to the treated volume falls in a range of about 20 Volt/mm to about 2000 Volt/mm.

4. An apparatus according to claim 1 wherein high voltage pulses are electrically balanced in such a manner that in average no direct current is passing through the treatment volume.

5. An apparatus according to claim 1 wherein high voltage pulses are rectangularly balanced.

6. A method for reducing deep subcutaneous fat deposits by electroporation comprising:

providing an applicator comprising a set of high voltage needle electrodes adapted for penetrating the skin of a patient and applying a high amplitude pulsed electric field to the area of the subcutaneous volume of tissues to be treated by electroporation, at least one of said plurality of needle electrodes including insulated portions and a pair of uninsulated needle portions axially separated along said needle electrode, wherein said uninsulated needle portions form axially separated electrodes of opposite polarity; and said insulated portions include proximal, distal, and central insulated portions, said proximal insulated portion being provided for insulating the skin of the patient during an electroporation treatment, said distal insulated portion being provided to avoid spark discharges to an adjacent needle electrode and said central insulated portion separating said electrodes, wherein said electrodes are disposed on said needle electrode such that they are disposed within the subcutaneous fat deposit during treatment;

providing a generator of high voltage pulses for applying pulsed electric field to the electrodes, said pulses generating an electric field above the upper electroporation limit for subcutaneous fat cells in the volume of the subcutaneous tissue to be treated;

connecting said generator of high voltage electrical pulses with corresponding needle electrodes placed in the deep subcutaneous fat tissue; and applying high voltage pulses via said set of needle electrodes with an amplitude sufficient to cause death to subcutaneous fat cells.

7. An apparatus for reducing deep subcutaneous fat deposits in a predetermined treatment volume beneath a predetermined area of a patient's skin by electroporation, said apparatus comprising:

a set of needle electrodes, wherein said set of electrodes comprises:

an array of electroporation needle electrodes, said electroporation needle electrodes being provided for applying a pulsed electric field to the subcutaneous volume of tissues, wherein said needle electrodes are arrayed such that each needle electrode is adjacent to at least one needle electrode having the opposite polarity and wherein the needle electrodes include proximal and distal insulated portions and a central uninsulated portion configured to insulate the skin and dispose the uninsulated portion in the subcutaneous fat deposit;

a generator of high voltage pulses for applying a pulsed electric field to the predetermined area via said electrode set, said pulses generating an electric field above the upper electroporation limit for subcutaneous fat cells in the volume of the subcutaneous tissue to be treated, and connectors connecting said generator of high voltage electrical pulses with corresponding electroporation electrodes.

8. An apparatus according to claim 7 wherein high voltage pulses are electrically balanced in such a manner that in average no direct current is passing through the treatment volume.

9. An apparatus according to claim 7 wherein high voltage pulses are [rectangular] *rectangularly* balanced.

10. Apparatus for reduction of subcutaneous fat deposits in a predetermined treatment zone beneath a predetermined area of a patient's skin by electroporation, said apparatus comprising:

a plurality of electrodes, wherein at least one of said electrodes is a subcutaneous electrode configured for placement under the skin and within the treatment zone and wherein at least one of said electrodes is a patch electrode applied to the patient's skin;

a generator of high voltage pulses for applying a pulsed electric field to the treatment zone via said electrodes, wherein the applied pulses generate an electric field above the upper electroporation limit for subcutaneous fat cells in the treatment zone, and connectors connecting said generator of high voltage electrical pulses with said electrodes.

11. An apparatus according to claim 10 wherein said subcutaneous electrode is a needle electrode adapted for penetrating the skin of a patient, said needle electrode including insulated portions and a pair of uninsulated needle portions axially separated alone said needle electrode, wherein said uninsulated needle portions form axially separate electrodes of opposite polarity; and said insulated portions include proximal, distal, and central insulated portions, said proximal insulated portion being provided for insulating the skin of the patient during an electroporation treatment, said distal insulated portion being provided to avoid spark discharaes to an adjacent needle electrode and said central insulated portion separating said electrodes, wherein said electrodes are disposed on said needle electrode such that they are disposed within the subcutaneous fat deposit during treatment.

12. An apparatus according to claim 10 wherein said apparatus includes at least a pair of subcutaneous electrodes.

13. An apparatus according to claim 12 wherein each of said at least one pair of subcutaneous electrodes is formed on a needle comprising proximal and distal insulated portions and wherein said subcutaneous electrode is formed therebetween said insulated portions on each needle.

14. An apparatus according to claim 10 and further including plurality of subcutaneous electrodes and wherein said plurality of subcutaneous electrodes comprises an array of electrodes each configured for placement under the skin and within the treatment zone, said electrodes being provided with alternating positive and negative polarities.

15. An apparatus according to claim 10 wherein the high voltage pulses are electrically balanced in such a manner that in average no direct current is passing through the treatment zone.

16. An apparatus according to claim 10 wherein the high voltage pulses are rectangularly balanced.

17. An apparatus according to claim 10 wherein said high voltage pulses have a duration in a range of about 10 microseconds to about 10 millisecond.

18. A method for reducing the number of subcutaneous fat cells in a predetermined treatment zone by electroporation of the cells in the treatment zone, said method comprising:

disposing at least a first electrode in the treatment zone;

disposing a second electrode on the patient's skin in close proximity to the first electrode; and applying high voltage electric field pulses via the first and second electrodes with an amplitude sufficient to cause death to subcutaneous fat cells by electroporation.

19. A method according to claim 18 wherein said at least one treatment zone electrode is a needle including an electrode.

20. A method according to claim 18 and further including a needle, wherein said plurality of electrodes comprises a pair of spaced apart electrodes disposed on said needle.

21. A method according to claim 18 wherein the high voltage pulses are electrically balanced in such a manner that in average no direct current is passing through the treatment zone.

22. An apparatus according to claim 17 wherein the amplitude of the electric field applied to the treated volume falls in a range of about 20 Volt/mm to about 2000 Volt/mm.

23. An apparatus according to claim 18 wherein said high voltage pulses have a duration in a range of about 10 microseconds to about 10 millisecond.

24. An apparatus according to claim 23 wherein the amplitude of the electric field applied to the treated volume falls in a range of about 20 Volt/mm to about 2000 Volt/mm.

* * * * *